United States Patent [19]

Leresche et al.

[11] Patent Number: 5,476,977
[45] Date of Patent: Dec. 19, 1995

[54] NAPHTHALENIC COMPOUND AND PROCESS FOR ITS PREPARATION

[75] Inventors: Jean-Paul Leresche, Preverenges; Yves Mentha, Geneva, both of Switzerland

[73] Assignee: Firmenich SA, Geneve, Switzerland

[21] Appl. No.: 286,732

[22] Filed: Aug. 5, 1994

Related U.S. Application Data

[63] Continuation of Ser. No. 39,014, Mar. 29, 1993, Pat. No. 5,396,014.

[30] Foreign Application Priority Data

Aug. 13, 1991 [CH] Switzerland ............... 02385/91

[51] Int. Cl.$^6$ .............................. C07C 13/48; C07C 2/66
[52] U.S. Cl. .................. 585/26; 585/24; 585/25; 585/411; 585/459
[58] Field of Search .................. 585/410, 411, 585/452, 459, 24, 25, 26

[56] References Cited

U.S. PATENT DOCUMENTS

| 4,284,818 | 8/1981 | Sato et al. | 568/323 |
| 4,551,573 | 11/1985 | Cobb | 585/459 |
| 4,877,916 | 10/1989 | Frank | 585/411 |

FOREIGN PATENT DOCUMENTS

0218138   4/1987   European Pat. Off. .

OTHER PUBLICATIONS

Chemical Abstracts: 104704t, vol. 99, 1983.

*Primary Examiner*—P. Achutamurthy
*Attorney, Agent, or Firm*—Pennie & Edmonds

[57] ABSTRACT

1,1,2,3,4,4,6-Heptamethyl-1,2,3,4-tetrahydronaphthalene, a novel naphthalenic compound, is useful as an intermediate for the preparation of 5,6,7,8-tetrahydro-3,5,5,6,7,8,8-heptamethyl-2-naphthalenecarbaldehyde. It is prepared by a process consisting of the addition of an olefin of formula

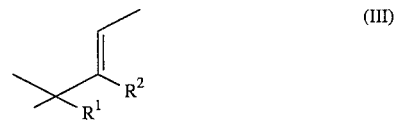

(III)

wherein $R^1$ and $R^2$ represent different substituents and each defines a hydrogen atom or a methyl radical, with p-cymene. 4,4-Dimethyl-2-pentene [compound (III): $R^1=CH_3$; $R^2=H$] is obtained by the co-metathesis reaction of an olefin of formula

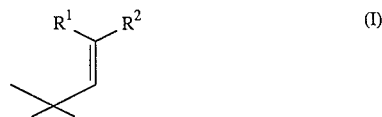

(I)

wherein $R^1$ and $R^2$ represent identical substituents designating each a hydrogen atom or a methyl radical, with an olefin of formula

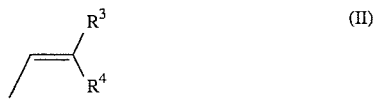

(II)

wherein $R^3$ and $R^4$ identical or different, designate each a hydrogen atom or a methyl radical in the presence of an appropriate catalyst consisting of $Re_2O_7$ on an inert solid carrier, or of $WCl_6/(C_2H_5))/Bu_4Sn$.

1 Claim, No Drawings

NAPHTHALENIC COMPOUND AND PROCESS FOR ITS PREPARATION

This is a continuation of application Ser. No. 08/039,014, filed Mar. 29, 1993, now U.S. Pat. No. 5,396,014.

TECHNICAL FIELD

The present invention relates to the field of organic synthesis. More particularly, it concerns a novel naphthalenic compound and its use as an intermediate product for the preparation of a prized perfuming ingredient.

PRIOR ART

Published European patent application No. 405 427-A2 describes a series of naphthalenic compounds of formula

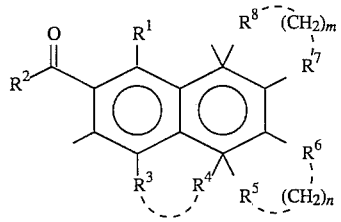

wherein
a) indexes m and n are identical and each defines an integer number equal to 0, symbols $R^1$ and $R^2$ are identical and represent each a hydrogen atom, or are different and represent each a hydrogen atom or a methyl radical, symbols $R^5$ and $R^8$ represent each a methyl radical, symbols $R^6$ and $R^7$, identical or different, represent each a hydrogen atom or a methyl radical, and either symbol $R^4$ represents a methyl radical and symbol $R^3$ a hydrogen atom or a methyl radical, or symbols $R^3$ and $R^4$ represent each a methylene radical belonging to a cycle as indicated by the dotted line, with the proviso that the following combinations are excluded:
1. $R^1=R^2=R^3=R^6=R^7=H$, or
2. $R^1=R^2=R^3=H$ and $R^6$ or $R^7=CH_3$, or
3. $R^2=CH_3$ and $R^3=R^6=R^7=H$, or
4. $R^2=CH_3$ and $R^3=H$ and $R^6$ or $R^7=CH_3$, or
5. $R^1=R^3=CH_3$, or
6. $R^3=R^4=CH_2$ and $R^2$ or $R^7=CH_3$; or wherein b) indexes m and n are distinct and define each an integer number equal to 0 or 1, symbol $R^2$ represents a hydrogen atom or a methyl radical, symbols $R^1$ and $R^3$ represent each a hydrogen atom, symbol $R^4$ represents a methyl radical and, either symbols $R^5$ and $R^6$ are identical (n=1) and represent each a methylene radical belonging to a cycle such as indicated by the dotted line, symbol $R^7$ representing a hydrogen atom and symbol $R^8$ a methyl radical, or symbol $R^5$ represents a methyl radical and symbol $R^6$ a hydrogen atom, symbols $R^7$ and $R^8$ being then identical (m=1) and representing each a methylene radical belonging to a cycle such as indicated by the dotted line.

These are compounds useful in perfumery, mainly as a result of their musky, amber and animal odor character. Amongst these compounds there is one preferentially used, owing to both the nature and the strength of its odor. It has in fact been ascertained that 5,6,7,8-tetrahydro-3,5,5,6,7,8,8-heptamethyl-2-naphthalenecarbaldehyde, as a result of its qualities, represents a prime perfuming ingredient.

In the above-mentioned European application, several synthetic methods for preparing this compound have been proposed but, considering its usefulness, it is not surprising to observe that its preparation has been the object of further research, which research has been aimed at improving the manufacturing costs.

DESCRIPTION OF THE INVENTION

The present invention is provided in this context. It brings in fact a novel solution of which there was no suggestion in the cited reference. It hinges on a critical element consisting of a useful intermediate of the synthesis of 5,6,7,8-tetrahydro-3,5,5,6,7,8,8-heptamethyl-2-naphthalenecarbaldehyde. Said intermediate is a hydrocarbon of formula

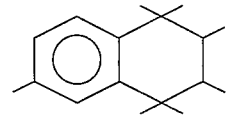

or 1,1,2,3,4,4,6-heptamethyl-1,2,3,4-tetrahydronaphthalene (hereafter designated as "HpMT"), which can be converted into the desired aldehyde via a formylation reaction according to the following reaction scheme:

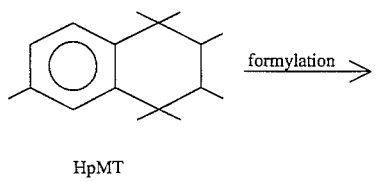

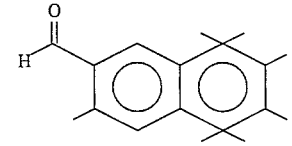

HpMT is a novel chemical entity which can be obtained, thanks to a process which is also the object of the invention, by reacting p-cymene and an olefin of formula

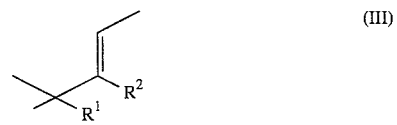

wherein $R^1$ et $R^2$ represent distinct substituents and each defines a hydrogen atom or a methyl radical. This is a reaction which can be carried out by analogy with known methods [see, to this effect: patent application JP 82 40420 -cf. C.A. 97, 38653 f]. It is based on the principle illustrated by way of the following reaction scheme:

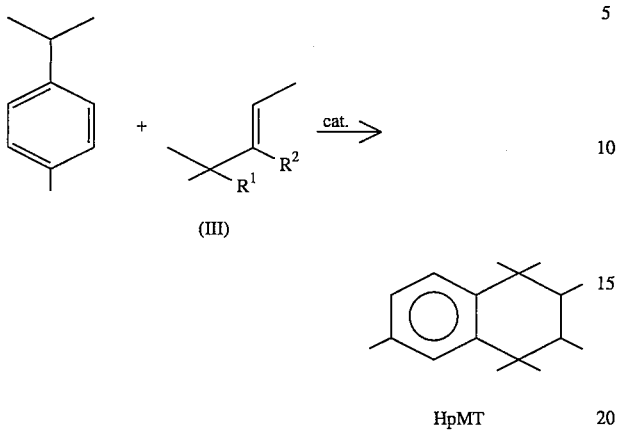

HpMT

The reaction takes place in the presence of catalytic amounts of aluminium chloride, to which there is optionally added iodine [cf. U.S. Pat. No. 4,551,573].

The concentration of $AlCl_3$ in the reaction mixture can vary in a fairly wide range of values; however, we observed that concentrations of the order of around 3–10 mole-%, relative to the quantity of olefin (III), made it possible to obtain the best yields. When concentrations below the lower limit indicated are used, the reaction proceeds too slowly, while with concentrations above the upper limit formation of undesired by-products, probably of indanic structure, is observed.

The relative proportions of the two reactants, p-cymene and olefin (III), also have a critical effect on the reaction's yield. Thus, when an excess of p-cymene relative to olefin (III) is used, HpMT can be obtained with theoretical yields above 60%. More particularly, a molar ratio of 2:1 p-cymene/olefin (III) provides the best yields.

The reaction can be carried out either in an inert organic solvent, preferably a chlorinated solvent such as dichloromethane or dichloroethane, or yet a cycloaliphatic hydrocarbon such as hexane, or in the absence of any solvent by direct mixture of the reactants.

For practical and economic reasons, the reaction is carried out at a temperature dose to room temperature, preferably at around 15° to 30° C.

An object of the present invention is therefore to provide a process for the preparation of 1,1,2,3,4,4,6-heptamethyl-1,2,3,4-tetrahydronaphthalene ("HpMT"), which process is characterized in that p-cymene is reacted with an olefin of formula

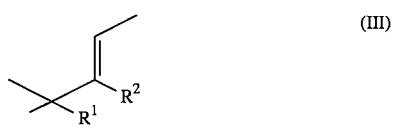

(III)

wherein $R^1$ and $R^2$ represent distinct substituents and each defines a hydrogen atom or a methyl radical, in a respective molar ratio equal or superior 1:1, in the presence of a catalytic system consisting of aluminium chloride or of a mixture of aluminium chloride and iodine, at a temperature comprised between about 0° and 30° C.

The HpMT thus obtained is in the form of a mixture of two diastereomers, in a cis/trans weight ratio of around 1:4.5.

Another object of the present invention is a process for the preparation of 4,4-dimethyl-2-pentene (hereafter designated as neoheptene), which process is based on the application of the so-called co-metathesis method [see for example: S. Warwel et al., Chem. Ztg 1983, 107, 115], more particularly of the reaction of olefins in the presence of appropriate catalysts.

The process for the preparation of neoheptene according to the invention is characterized in that an olefin of formula

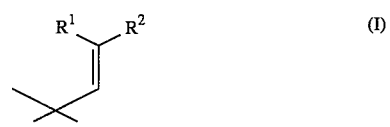

(I)

wherein $R^1$ and $R^2$ represent identical substituents designating each a hydrogen atom or a methyl radical, is subjected to co-metathesis with an olefin of formula

(II)

wherein $R^3$ and $R^4$, identical or distinct, designate each a hydrogen atom or a methyl radical, via contact of said olefins, at a temperature comprised between about 30° and 100° C., with a catalytic system consisting of $Re_2O_7$ on an inert solid carrier, or of $WCl_6/(C_2H_5)_2O/Bu_4Sn$.

Although it was known that neohexene [compound (I): $R^1=R^2=H$] underwent co-metathesis reactions, namely with 5-decene and 9-octadecene—see S. Warwel et al., cited ref.—, the application of this type of reaction to obtain neoheptene has not been reported in the prior art. This is all the more surprising because numerous have been the syntheses proposed up to now for obtaining this olefin.

As indicated above, and depending on the nature of the various substituents, formula (I) can represent neohexene ($R^1=R^2=H$) or 2,4,4-trimethyl-2-pentene ($R^1=R^2=CH_3$), while formula (II) can represent propene ($R^3=R^4=H$), or 2-methyl-2-butene ($R^3=R^4=CH_3$), or yet 2-butene ($R^3=CH_3$; $R^4=H$ or $R^3=H$; $R^4=CH_3$).

The reaction which characterizes the process of the invention is illustrated by the following reaction scheme:

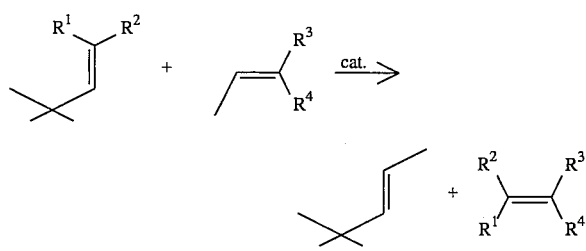

Depending on the nature of the reactants used, the reaction can be carried out at either atmospheric pressure or at a pressure above the latter. When using olefins having a boiling point which, at ordinary pressure, is below room temperature, the reaction will be carried out under pressure, preferably in an autoclave, while with reactants such as, for example, neohexene and 2-methyl-2-butene, the reaction can take place at atmospheric pressure.

As the catalyst, $Re_2O_7$ on a solid carrier has been mentioned above. Alumina is a perfectly convenient solid support. It has also been noticed that it was possible to increase the activity of the catalyst by adding to the latter alkylated tin derivatives, for example tetrabutyltin.

The respective proportions of the catalyst and olefins vary in a wide range of values. They are preferably comprised between about 0.05 et 0.5 mole-%, while the molar amount of $Re_2O_7$, for example relative to adjuvant $Bu_4Sn$, can be of the order of about 1:1 to 1:2. The content of $Re_2O_7$ in the mixture with alumina was of the order of 3–10%, preferably of 5 to 7%, parts by weight.

The invention is illustrated in further detail by way of the following examples wherein the temperatures are indicated in degrees centigrade and the abbreviations have the usual meaning in the art.

Preparation and (Re)activation of the $Re_2O_7/Al_2O_3$ catalyst

A solution of 10 g of rhenium (VII) oxide (Fluka 83680) in 600 ml of water is charged into a 2 l flask. 170 G of gamma alumina (Akzo-Ketjen 001-3P) is added thereto and the mixture is stirred by means of a Rotavapor during 3 h. Water is then evaporated under reduced pressure and the impregnated gamma alumina is pre-dried at 120° under 10 mbar for 1 h. After calcination (see below), 162.4 g of $Re_2O_7/Al_2O_3$ (6.16%) are obtained.

The activation of the catalyst, which must be repeated after each utilisation, is carried out as follows. The catalyst is charged into a quartz tube (int. diam.=25 mm) and is heated to 550° under a slight flow of air during 3 h. The temperature is then increased to 600° and the flow of air replaced by a nitrogen flow. After 30 min at this temperature, it is allowed to cool down, still under a flow of nitrogen. The catalyst ready to use is stocked under inert atmosphere. This process was carried out upon each of the experiments described in the following examples.

EXAMPLE 1

PREPARATION OF NEOHEPTENE

A 3-neck flask equipped with a thermometer and a water condenser, topped successively with a column (int. diam.=25 mm, length=20 cm) filled with Raschig rings (diam.=6 mm, length=6 mm), a double-mantle condenser connected to a cryostat, then a bubbler, was charged with 162 g of $Re_2O_7/Al_2O_3$ (6.16%, i.e. 20.7 mmole of $Re_2O_7$) under a counter-flow of nitrogen. 870 G (10.35 mole) of neohexene (Philips Petroleum), 725 g (10.35 mole) of 2-methyl-2-butene (Shell) and 14.4 g (41.2 mmole) of tetrabutyltin (Fluka 86942) were added thereto. The cryostat temperature is adjusted to −12° and the flask is plunged in a bath at 45°. Boiling, reflux in the Raschig column and the release of isobutylene indicate that the reaction has started. The temperature of the reaction mixture, initially at 27°, increases slowly. After 6.8 h of reaction, it is at 37°. The reaction mixture is cooled down, then filtered, and 1213 g of raw product are obtained. GC analysis shows that it contains 22% of 2-methyl-2-butene, 14% of neohexene and 56% of neoheptene. The GC raw yield is 67%. Calculated relative to the consumed neohexene, it is 83%. Fractional distillation allows the recovery of the unreacted starting olefins (b. p. 39°–41°), then of pure neoheptene (b.p. 76°).

EXAMPLE 2

PREPARATION OF NEOHEPTENE

A 250 ml Berghof autoclave was charged with 9.7 g of $Re_2O_7/Al_2O_3$ (5%) (i.e. 1.0 mmole $Re_2O_7$), 34.0 g (0.40 mole) of neohexene and 0.69 g (2.0 mmole) of $Bu_4Sn$. The autoclave is closed and a slight depression is installed, then about 37 g (0.66 mole, 1.6 eq.) of trans-2-butene (Fluka 19111) are introduced. The mixture is heated to 55°±5° for 2.0 h, under moderate stirring. The autoclave is then cooled and a cold trap (water+ice) is connected to the gas outlet valve. The latter is then opened to allow the escape of the excess 1-butene, as well as of the formed gases (ethylene, propylene). The remaining liquid phase is filtered and there are thus obtained (including the trap-content) 38.9 g of raw mixture. GC analysis shows that it contains 15% of 2-butene, 16% of neohexene and 56% of neoheptene. The raw GC yield is therefore 55.5%. Based on consumed neohexene, it is 67%.

EXAMPLE 3

PREPARATION OF NEOHEPTENE

A 250 ml Berghof autoclave is charged with 34.7 g (0.41 mole) of neohexene, 1.8 g (5.2 mmole) of $Bu_4Sn$ and 0.20 g (2.7 mmole) of diethylether. Stirring (magnetic bar) is switched on and 1.0 g (2.5 mmole) of $WCl_6$ (Fluka 95400) is added under a counter-flow of nitrogen. The autoclave is closed and a slight depression installed, then about 34.7 g (0.62 mole, 1.5 eq.) of trans-2-butene are introduced. The mixture is heated to 100°±10° for 90 min, under vigorous stirring. The autoclave is then cooled and the gas outlet valve is opened to ls allow excess 2-butene and the formed gases (ethylene, propylene) to escape. To the remaining liquid phase one adds 30 ml of a 10% aqueous solution of NaOH. The phases are separated and the organic phase is washed with a further 30 ml of 10% aqueous NaOH, 30 ml of 5% aqueous HCl, 30 ml of water and finally 30 ml of saturated aqueous NaCl. After drying over sodium sulfate and filtration, there are obtained 38.3 g of raw mixture. A GC analysis shows that it contains 12% of 2-butene, 20% of neohexene and 55% of neoheptene. The raw GC yield is thus 52%. Based on consumed neohexene, it is 67%.

EXAMPLE 4

PREPARATION OF HpMT

A 100 ml 3-neck flask equipped with a thermometer, a condenser topped with a nitrogen bubbler, an inlet funnel and a magnetic stirrer, was charged with 25 ml of dry dichloromethane and 0.80 g (0.006 mole) of finely divided aluminium chloride (Fluka 06220). The mixture is cooled to 15° and a mixture of 32.2 g (0.24 mole) of p-cymene with 11.8 g (0.12 mole) of neoheptene is added thereto over 40 min, while maintaining the temperature at 15°±2°. Once the addition is completed, the reaction mixture is allowed to return to room temperature and stirring is continued for a further 3 h. The reaction mixture is cooled to about 5° before adding thereto 50 ml of cold water. After separating the phases, the aqueous phase is extracted with diethyl ether, then the combined organic phases are washed with 50 ml of water and 50 ml of saturated aqueous NaCl, then dried over sodium sulfate and concentrated on the Rotavapor. 35.2 G of raw product, containing (GC) 21.7% of HpMT and 63.6% of p-cymene, is thus obtained. A 3.0 g portion is bulb-to-bulb distilled and provides a first fraction of 1.85 g of p-cymene (95% GC) and a second fraction of 1.07 g containing 11.6% cis and 55.1% trans-HpMT. The rate of residue is thus below 3% and the reaction yield, based on the neoheptene consumed, is 60.5%. A sample of pure trans-1,1,2,3,4,4,6-heptamethyl-1,2,3,4-tetrahydronaphthalene, m.p.=65°–66°, was obtained by crystallization from a mixture AcOEt/EtOH (1:1).

MS: 230(M$^+$, 12%), 215(38), 173(56), 159(100), 141(14), 131(43), 57(84), 41(17), $^1$H-NMR(360 MHz, CDCl$_3$): 0.96(d, J=5.49 Hz, 6H); 1.08(s, 3H); 1.09(s, 3H); 1.29(s, 3H); 1.31(s, 3H); 1.58(m, 2H); 2.30(s, 3H); 6.96(dd, J=7.93 and 1.83 Hz, 1H); 7.15(d, J=1.83 Hz, 1H); 7.25(d, J=7.93, 1H) δ ppm $^{13}$C-NMR(90.54 MHz, CDCl$_3$): 13.79(q, 2 CH$_3$), 21.09(q), 25.59(q), 25.62(q), 29.52(q), 29.61(q), 37.55(s), 37.79(s), 39.41(d, 2CH), 126.51(d), 127.09(d), 127.60(d), 134.53(s), 142.68(s), 145.46(s) IR(KBr): 2973(strong), 1662(s), 1458(medium), 1208(m), 1168(m), 824(m) cm-1

Other specific examples of the preparation of HpMT are summarized in the following table [a]:

| Exp. | p-cym (mole) | AlCl$_3$ (mole) | Solvent | Amount of solvent | T (°C.) | Yield (%) |
|---|---|---|---|---|---|---|
| 1) | 0.135 | 0.006 | CH$_2$Cl$_2$ | 25 ml | 15→25 | 54 |
| 2) | 0.135 | 0.006 | CH$_2$Cl$_2$ | 0.06 mole | 15→25 | 41 |
| 3) | 0.135 | 0.006 | (ClCH$_2$)$_2$ | 25 ml | 15→25 | 56 |
| 4) | 0.135 | 0.006 | (ClCH$_2$)$_2$ | 0.06 mole | 15→25 | 40 |
| 5) | 0.135 | 0.006 | cyclohexane | 25 ml | 15→25 | 43 |
| 6) | 0.135 | 0.006 | — | — | 15→25 | 39 |
| 7) | 0.135 | 0.030 | CH$_2$Cl$_2$ | 25 ml | 15→25 | <5 |
| 8) | 0.135 | 0.0012 | CH$_2$Cl$_2$ | 25 ml | 15→25 | 19 |
| 9) | 0.060 | 0.006 | CH$_2$Cl$_2$ | 25 ml | 15→25 | 47 |
| 10) | 0.135 | 0.006 | CH$_2$Cl$_2$ | 25 ml | 0 | 50 |
| 11) | 0.135 | 0.006 | CH$_2$Cl$_2$ | 25 ml | 25 | 54 | a) reactions with 0.12 mole of neoheptene (4,4-dimethyl-2-pentene).

The results obtained in the preceding examples, as well as in other specific examples of the preparation of neoheptene are resumed in the following table:

$$A + B \rightleftharpoons \text{Neoheptene} + \text{byproduct}$$

where A bears substituents $R^1, R^2$ and B bears $R^3, R^4$.

| Exp. | R$^1$ | R$^2$ | R$^3$ | R$^4$ | Cat. | Cat/A (weight) | B/A | Time (h) | Temp. (°C.) | Conv. (%) | Yield (%) |
|---|---|---|---|---|---|---|---|---|---|---|---|
| 1) | H | H | H | H | I | 0.2 | 1.0 | 10 | 40 | 25.7 | 26 |
| 2) | CH$_3$ | CH$_3$ | CH$_3$ | H | I | 0.4 | 4.8 | 5 | 40 | 93.3 | 59 |
| 3) | CH$_3$ | CH$_3$ | CH$_3$ | H | I | 0.8 | 2.4 | 6 | 40 | 99.4 | 59 |
| 4) | CH$_3$ | CH$_3$ | CH$_3$ | H | II | 0.8 | 7.6 | 3 | 40 | 99.6 | 87 |
| 5) | H | H | CH$_3$ | CH$_3$ | III | 0.2 | 1.0 | 7 | 27–37 | 81 | 67 |
| 6) | H | H | CH$_3$ | CH$_3$ | IV | 0.15 | 1.0 | 3 | 40 | | 0 |
| 7) | H | H | CH$_3$ | H | III | 0.3 | 1.6 | 2 | 55 | 82 | 55 |
| 8) | H | H | CH$_3$ | H | IV | 0.08 | 1.5 | 1.5 | 100 | 77 | 52 |
| 9) | CH$_3$ | CH$_3$ | CH$_3$ | H | IV | 0.10 | 3.7 | 3 | 80 | | 0 |

I = Re$_2$O$_7$/Al$_2$O$_3$
II = Re$_2$O$_7$/Al$_2$O$_3$ + Me$_4$Sn
III = 5–7% Re$_2$O$_7$/Al$_2$O$_3$ + Bu$_4$Sn; (Re$_2$O$_7$:Bu$_4$Sn:olefins = 1:2:1000)
IV = WCl$_6$ — Et$_2$O — Bu$_4$Sn; (WCl$_6$:Et$_2$O:Bu$_4$Sn:olefins = 1:1:2:500)

We claim:
1. 1,1,2,3,4,4,6-Heptamethyl-1,2,3,4-tetrahydronaphthalene.

* * * * *